(12) United States Patent
Hartley (10) Patent No.: US 7,722,657 B2
(45) Date of Patent: May 25, 2010

(54) ASYMMETRIC STENT GRAFT ATTACHMENT

(75) Inventor: David Ernest Hartley, Subiaco (AU)

(73) Assignees: William A. Cook Australia Pty. Ltd., Queensland (AU); Cook Incorporated, Bloomington, IN (US); William Cook Europe ApS, Bjaeverskoy (DK)

( * ) Notice: Subject to any disclaimer, the term of this patent is extended or adjusted under 35 U.S.C. 154(b) by 1023 days.

(21) Appl. No.: 10/647,642

(22) Filed: Aug. 25, 2003

(65) Prior Publication Data

US 2004/0073289 A1 Apr. 15, 2004

Related U.S. Application Data

(60) Provisional application No. 60/405,367, filed on Aug. 23, 2002.

(51) Int. Cl.
*A61F 2/06* (2006.01)

(52) U.S. Cl. .................................... 623/1.13; 623/1.29

(58) Field of Classification Search ............... 623/1.11, 623/1.12
See application file for complete search history.

(56) References Cited

U.S. PATENT DOCUMENTS

| | | | | |
|---|---|---|---|---|
| 4,913,141 A | * | 4/1990 | Hillstead | 623/1.11 |
| 5,387,235 A | * | 2/1995 | Chuter | 623/1.11 |
| 5,480,423 A | * | 1/1996 | Ravenscroft et al. | 623/1.11 |
| 5,562,726 A | * | 10/1996 | Chuter | 623/1.35 |
| 5,575,817 A | | 11/1996 | Martin | |
| 5,634,941 A | * | 6/1997 | Winston et al. | 623/1.11 |
| 5,653,743 A | | 8/1997 | Martin | |
| 5,720,776 A | | 2/1998 | Chuter et al. | |
| 5,741,325 A | | 4/1998 | Chaikof et al. | |
| 5,843,160 A | | 12/1998 | Rhodes | |
| 5,873,906 A | * | 2/1999 | Lau et al. | 128/898 |
| 6,036,723 A | | 3/2000 | Anidjar et al. | |
| 6,102,938 A | | 8/2000 | Evans et al. | |
| 6,206,931 B1 | | 3/2001 | Cook et al. | |
| 6,224,609 B1 | | 5/2001 | Ressemann et al. | |
| 6,331,191 B1 | | 12/2001 | Chobotov | |
| 2001/0004707 A1 | | 5/2001 | Dereume et al. | |
| 2001/0014823 A1 | | 8/2001 | Ressemann et al. | |
| 2001/0049554 A1 | | 12/2001 | Ruiz et al. | |
| 2003/0120332 A1 | | 6/2003 | Hartley | |

(Continued)

FOREIGN PATENT DOCUMENTS

EP 0680733 11/1995

(Continued)

OTHER PUBLICATIONS

International Search Report; PCT/US03/26561; Dec. 2003.

*Primary Examiner*—Corrine M McDermott
*Assistant Examiner*—Christopher D Prone
(74) *Attorney, Agent, or Firm*—Richard J. Godlewski (57) ABSTRACT

An arrangement for mounting a stent graft prosthesis (1) onto a deployment device (2) with a retention arrangement (3) which includes retention at a number of points of the circumference of the proximal end of the stent graft prosthesis (1). The arrangement provides a greater circumferential distance (13) between two adjacent retention points (9) then other of the points. When the deployment device is deployed in a curved lumen such as the thoracic arch it is oriented so that the greater circumferential distance (13) is on the inner side of the curve.

1 Claim, 4 Drawing Sheets

U.S. PATENT DOCUMENTS

| | | |
|---|---|---|
| 2003/0233140 A1 | 12/2003 | Hartley et al. |
| 2004/0054396 A1 | 3/2004 | Hartley et al. |
| 2004/0082990 A1 | 4/2004 | Hartley |
| 2004/0098079 A1 | 5/2004 | Hartley et al. |

FOREIGN PATENT DOCUMENTS

| | | |
|---|---|---|
| WO | 9526695 | 10/1995 |
| WO | 9853761 | 12/1998 |
| WO | 9929262 | 3/1999 |
| WO | 03034948 | 5/2003 |

* cited by examiner

ASYMMETRIC STENT GRAFT ATTACHMENT

CROSS-REFERENCE TO RELATED APPLICATIONS

This application claims priority of provisional application Ser. No. 60/405,367, filed Aug. 23, 2002.

TECHNICAL FIELD

This invention relates to deployment of endovascular stent grafts and in particular the deployment of endovascular stent grafts into lumens in the human or animal body such as into the thoracic arch region of the aorta.

BACKGROUND OF THE INVENTION

This specification will be discussed in relation to its application to treatment of aortic arch disease, that is to treatment in the thoracic arch of a patient but the invention is not so limited and is applicable to any lumen of the human or animal body and particularly curved lumens.

Throughout this specification the term distal with respect to a portion of the aorta, a deployment device or a prosthesis such as a stent graft is intended to mean the end of the aorta, deployment device or from the heart and the term proximal is intended to mean the portion of the aorta, deployment device or end of the prosthesis nearer to the heart. For other lumens within the human or animal body the terms caudal and cranial respectively should be understood.

When deploying a stent graft which is substantially cylindrical in a curved aorta there is a danger that the proximal end of the stent graft, that is the end nearer the heart, will not lie flat against the walls of a aorta and blood flow can get underneath the edge of the graft particularly on the inner side of the curve of the thoracic arch and cause the stent graft to buckle and close off thereby causing serious problems.

SUMMARY OF THE INVENTION

It is the object of this invention to provide a method and arrangement for mounting a stent graft onto a deployment device and deploying the stent graft in an attempt to overcome the above problems.

In one form therefore, although this may not necessarily be the only or broadest form the invention is said to reside in a stent graft prosthesis mounted to a deployment device and adapted to be deployed in a curved lumen, the curved lumen having an inner side and an outer side of the curve, the stent graft prosthesis being temporarily mounted to the deployment device at at least one end of the prosthesis by a retention arrangement, the retention arrangement of the stent graft prosthesis including a retention to the deployment device at a plurality of points of the circumference of the proximal end of the stent graft prosthesis, there being a greater circumferential distance between two adjacent retention points then other of the points, whereby when the deployment device is deployed in the curved lumen the greater circumferential distance is on the inner side of the curve.

Preferably the retention arrangement includes a fastening to a release mechanism at at least two points of the circumference of the prosthesis whereby a larger and a smaller fold of the graft material is formed.

More preferably three retention points may be used so that one larger and two smaller folds of the graft material are formed.

In an alternative form the invention is said to reside in a deployment device and stent graft prosthesis temporarily mounted thereto and adapted to be deployed in a curved lumen, the curved lumen having an inner side and an outer side of the curve, the deployment device including a deployment catheter and a release mechanism, the stent graft prosthesis comprising a tube of graft material having a first end and a second end and being mounted to the deployment device at at least its first end by a retention arrangement, the retention arrangement including a retention to the deployment device at a plurality of points of the circumference of the proximal end of the stent graft prosthesis, there being a greater circumferential distance between two adjacent retention points then other of the points, and the retention points being provided by the release mechanism being engaged with the graft material, whereby when the deployment device is deployed in the curved lumen the greater circumferential distance is on the inner side of the curve.

Preferably the retention arrangement includes a fastening to a release mechanism at at least two points of the circumference of the prosthesis whereby a larger and a smaller fold of the graft material is formed. Alternatively there may be three retention points so that one larger and two smaller folds or loops of the graft material are formed. Hence in this form the retention arrangement provides one larger fold and at least one smaller fold of the proximal end of the graft material wherein the larger fold is on the inner side of the curve when the deployment device is deployed in the curved lumen.

Preferably the deployment catheter includes a guide wire catheter and a trigger wire catheter coaxially around the guide wire catheter and the release mechanism includes trigger wires passing along the annular space between the guide wire catheter and the trigger wire catheter and exiting through apertures in the trigger wire catheter.

The apertures may be equally spaced around the trigger wire catheter.

Preferably the trigger wires are engaged to the graft material by loops of thread-like material and the loops of thread-like material are adapted to remain with the graft material after deployment.

Alternatively the trigger wires may engage directly with the graft material.

Preferably the stent graft prosthesis includes stents of a self expanding type being zig zag Z stents and the tube graft material and the retention is by sutures tied to trigger wires on the deployment device and around bends of the zig zag Z stents on the stent graft prosthesis.

Further retention points may be provided along the length of the stent graft prosthesis such as at the second end of the stent graft prosthesis.

In an alternative form the invention is said to reside in a method of mounting of a stent graft prosthesis to a deployment device for deployment of the stent graft prosthesis in to a curved lumen having an inner side and an outer side of the curve, the method including the step of mounting the stent graft prosthesis to a deployment device so that a first end and a second end of the prosthesis are separately retained to the deployment device, the retention at the first end being by the stent graft prosthesis being retained at a plurality of points of the circumference of the stent graft prosthesis to the deployment device, there being a greater circumferential distance between the two adjacent retention points than others of the retention points and whereby in use the greater circumferential distance is placed on the inner side of the curve.

Preferably the retention is by fibres such as sutures tied to trigger wires on a deployment device but other forms of retention such as by direct engagement of the trigger wires into fabric of the stent graft is also within the scope of the invention.

The retention is preferably at three points around the circumference of the first end of the stent graft prosthesis.

Preferably the stent graft is a type which includes stents which are zig zag Z stents covered by a graft material.

Preferably the retention is by sutures tied to trigger wires on the deployment device and around bends of the zig zag Z stents on the stent graft.

Preferably the deployment device comprises a guide wire catheter and a trigger wire catheter coaxially around the guide wire catheter with trigger wires passing along the annular space between the guide wire catheter and the trigger wire catheter and exiting through apertures at the retention points. The apertures may be equally spaced around the trigger wire catheter or they may be spaced at other selected spacings.

Further retention points may be provided along the length of the stent graft such as at the distal end of the stent graft.

In a further form the invention is said to reside in a method of deploying a stent graft prosthesis in the thoracic arch of a patient, the thoracic arch having a curvature defining an inner curve and an outer curve, the stent graft prosthesis being mounted on a deployment device under a slidable sheath and being retained to the deployment device at at least a proximal end of the stent graft prosthesis, the proximal retention being provided by retention at a number of points around the circumference of the stent graft prosthesis to provide a plurality of folds between the retention points so that one of the folds of graft material between adjacent retention points is larger than other of the folds, the method of deploying including the steps of deploying the deployment device into the aorta such that the larger of the folds of the graft material is adjacent to the inner curve, withdrawing the sheath to allow the stent graft prosthesis to expand under the influence of self expanding stents except at the proximal end so that blood flows through the larger fold at the proximal end into the interior of the stent graft prosthesis, releasing the proximal end of the stent graft prosthesis thereby allowing the graft to fully expand against the walls of the aorta and withdrawing the deployment device.

It will be seen that by this arrangement blood flow through the larger fold of the proximal end of the graft will cause that side of the graft to engage against the wall of the aorta so that upon subsequent release of the entire stent graft, the stent graft will correctly engage against the walls of the aorta in the thoracic arch.

In a still further form the invention is said to reside in a method of deploying a stent graft prosthesis in the thoracic arch of a patient, the thoracic arch having a curvature defining an inner curve and an outer curve, the stent graft prosthesis having a distally extending exposed stent and being mounted on a deployment device under a slidable sheath and being retained to the deployment device at a proximal end of the stent graft prosthesis and the distally extending exposed stent being retained in a capsule on the deployment device, the proximal retention being provided by retention at a number of points around the circumference of the stent graft prosthesis to provide a plurality of folds between the retention points so that one of the folds of graft material between adjacent retention points is larger than other of the folds, the method of deploying including the steps of deploying the deployment device into the aorta such that the larger of the folds of the graft material is adjacent to the inner curve, withdrawing the sheath to allow the stent graft prosthesis to expand under the influence of self expanding stents except at the proximal end so that blood flows through the larger fold at the proximal end into the interior of the stent graft prosthesis, withdrawing the capsule to release the distally extending exposed stent, releasing the proximal end of the stent graft prosthesis thereby allowing the graft to fully expand against the walls of the aorta and withdrawing the deployment device.

In an alternative form the invention is said to reside in a deployment device for deploying a stent graft prosthesis into a thoracic arch of a patient, the stent graft prosthesis being temporarily mounted to the deployment device and adapted to be deployed in the thoracic arch, the thoracic arch having a curved lumen having an inner side and an outer side of the curve, the stent graft prosthesis being mounted to the deployment device at least the proximal end of the prosthesis by a retention arrangement, the retention arrangement including a retention to the deployment device at a plurality of points of the circumference of the proximal end of the stent graft prosthesis, there being a greater circumferential distance between two adjacent retention points then other of the points, whereby when the deployment device is deployed in the curved lumen the greater circumferential distance is on the inner side of the curve.

In a further alternative form the invention is said to reside in an introducer for introducing a stent graft prosthesis into a curved lumen of a patient, the introducer including an arrangement for temporarily fixing the prosthesis to the introducer while it is being introduced into the lumen, wherein three or more positions on one end of the prosthesis are to be fixed to the arrangement, wherein the circumferential distance between two adjacent ones of those positions is greater than the circumferential distance between other adjacent positions of those positions and wherein the introducer serves to introduce the prosthesis into the lumen with said two adjacent positions next to the inner side of the curve of the lumen.

BRIEF DESCRIPTION OF THE DRAWING

This then generally describes the invention but to assist with understanding, reference will now be made to the accompanying drawings which show preferred embodiments of the invention.

DETAILED DESCRIPTION

U.S. Pat. No. 5,387,235 entitled "Endovascular Transluminal Prosthesis For Repair Of Aneurysms" discloses apparatus and methods of retaining grafts onto deployment devices. These features and other features disclosed in U.S. Pat. No. 5,387,235 could be used with the present invention and the disclosure of U.S. Pat. No. 5,387,235 is herewith incorporated in its entirety into this specification.

U.S. Pat. No. 5,720,776 entitled "Stent Barb" discloses improved barbs with various forms of mechanical attachment to a stent. These features and other features disclosed in U.S. Pat. No. 5,720,776 could be used with the present invention and the disclosure of U.S. Pat. No. 5,720,776 is herewith incorporated in its entirety into this specification.

U.S. Pat. No. 6,206,931 entitled "Graft Prosthesis Materials" discloses graft prosthesis materials and a method for implanting, transplanting replacing and repairing a part of a patient and particularly the manufacture and use of a purified, collagen based matrix structure removed from a submucosa tissue source. These features and other features disclosed in U.S. Pat. No. 6,206,931 could be used with the present invention and the disclosure of U.S. Pat. No. 6,206,931 is herewith incorporated in its entirety into this specification.

PCT Patent Publication No. WO98/53761 entitled "A Prosthesis and a Method of Deploying a Prosthesis" discloses an introducer for a prosthesis which retains the prosthesis so that each end can be moved independently. These features and other features disclosed in PCT Patent Publication No. WO98/53761 could be used with the present invention and the disclosure of PCT Patent Publication No. WO98/53761 is herewith incorporated in its entirety into this specification.

PCT Patent Publication No. WO99/29262 entitled "Endoluminal Aortic Stents" discloses a fenestrated prosthesis for placement where there are intersecting arteries. This feature and other features disclosed in PCT Patent Publication No. WO99/29262 could be used with the present invention and the disclosure of PCT Patent Publication No. WO99/29262 is herewith incorporated in its entirety into this specification.

PCT Patent Publication No. WO03/034948 entitled "Prostheses for Curved Lumens" discloses prostheses with arrangements for bending the prosthesis for placement into curved lumens. This feature and other features disclosed in PCT Patent Publication No. WO03/034948 could be used with the present invention and the disclosure of PCT Patent Publication No. WO03/034948 is herewith incorporated in its entirety into this specification.

U.S. Provisional Patent Application No. 60/392,682 entitled "Trigger Wires" discloses release wire systems for the release of stent grafts retained on introducer devices. This feature and other features disclosed in U.S. Provisional Patent Application No. 60/392,682 could be used with the present invention and the disclosure of U.S. Provisional Patent Application No. 60/392,682 is herewith incorporated in its entirety into this specification.

U.S. Provisional Patent Application No. 60/392,667 entitled "Thoracic Deployment Device" discloses introducer devices adapted for deployment of stent grafts particularly in the thoracic arch. This feature and other features disclosed in U.S. Provisional Patent Application No. 60/392,667 could be used with the present invention and the disclosure of U.S. Provisional Patent Application No. 60/392,667 is herewith incorporated in its entirety into this specification.

U.S. Provisional Patent Application No. 60/391,737 entitled "A Stent-Graft Fastening Arrangement" discloses arrangements for fastening stents onto grafts particularly for exposed stents. This feature and other features disclosed in U.S. Provisional Patent Application No. 60/391,737 could be used with the present invention and the disclosure of U.S. Provisional Patent Application No. 60/391,737 is herewith incorporated in its entirety into this specification.

PCT Patent Publication No. WO03/053287 entitled "Improving Graft Adhesion" discloses arrangements on stent grafts for enhancing the adhesion of such stent grafts into walls of vessels in which they are deployed. This feature and other features disclosed in PCT Patent Publication No. WO03/053287 could be used with the present invention and the disclosure of PCT Patent Publication No. WO03/053287 is herewith incorporated in its entirety into this specification.

U.S. Provisional Patent Application No. 60/405,769 entitled "Composite Prostheses" discloses prostheses or stent grafts suitable for endoluminal deployment. These prostheses and other features disclosed in U.S. Provisional Patent Application No. 60/405,769 could be used with the present invention and the disclosure of U.S. Provisional Patent Application No. 60/405,769 is herewith incorporated in its entirety into this specification. Now looking more closely at the drawings and in particular FIGS. 1 to 2.

Figure 1:
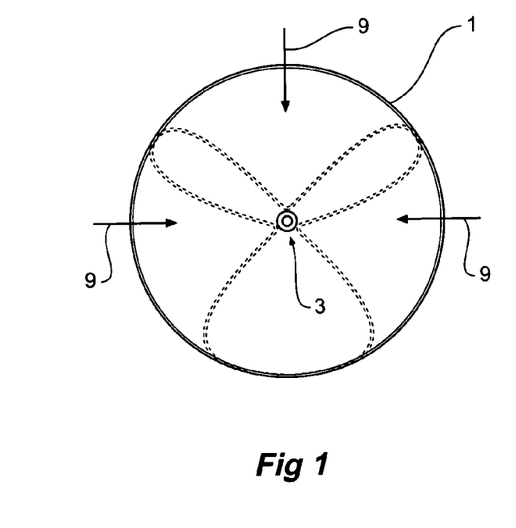
FIG. 1 shows a front on view of a stent graft showing where the retention points may be placed in one embodiment of the invention.
Figure 2:
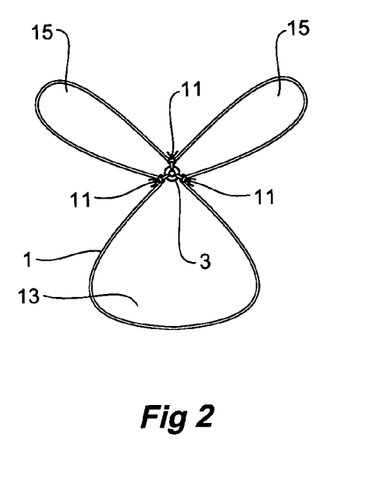
FIG. 2 shows the embodiment in FIG. 1 after attachment of the retention points to trigger wires.

Now looking more closely at the drawings and in particular FIGS. 1 to 2.

It will be seen from an end on view of the stent graft prosthesis that in its unrestrained state, as particularly shown in FIG. 1, it has a substantially circular body end 1. A deployment device for such a stent graft prosthesis has towards its proximal end a retention arrangement 3 for the retention of the proximal end of the stent graft body end 1 to the deployment device, the mechanism for which will be discussed in detail in relation to FIGS. 3 to 5. The retention arrangement 3 engages various points around the circumference of the stent graft body end 1 to the deployment device to give the asymmetric arrangement as shown in FIG. 2.

To provide the stent graft retention of the present invention, points of the circumference of the graft 1 as shown by the arrows 9 in FIG. 1 are drawn towards the retention arrangement 3 and retained by thread-like material 11 such as fibres or suture material so that the end on view of the stent graft becomes substantially as shown in FIG. 2. In this embodiment there are three retention points but other numbers of retention points may also be used. This asymmetric arrangement of stent graft attachment produces a larger fold 13 and two smaller folds 15. It will be noted, too, that the larger circumferential portion of the proximal end of the graft produces the larger fold 13 and the smaller circumferential portions of the proximal end of the graft produce the smaller folds 15.

Figure 3:
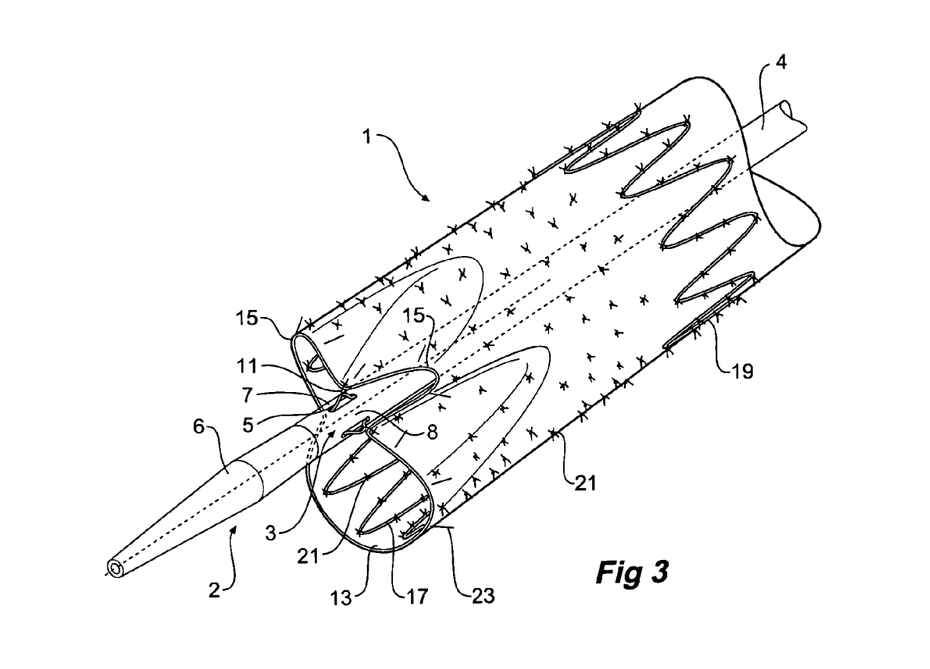
FIG. 3 shows a schematic view of a retention arrangement for a stent graft onto a deployment device according to one embodiment of the invention.
Figure 4:
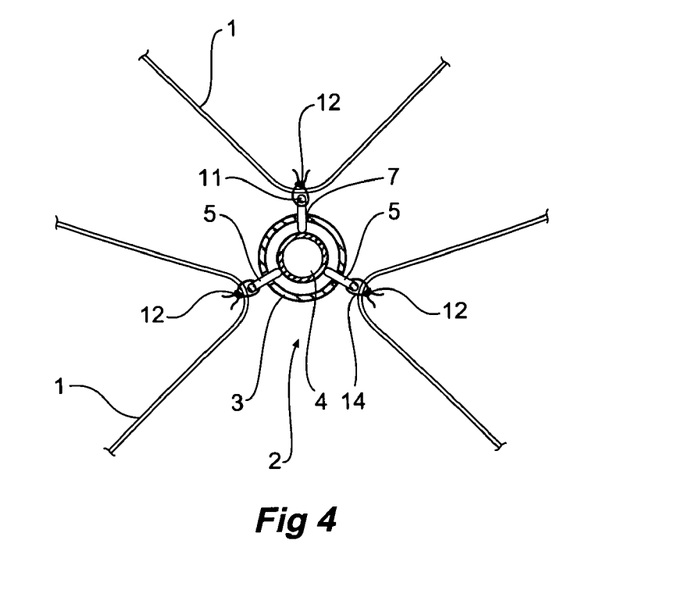
FIG. 4 shows a detailed transverse part cross section of the embodiment of FIG. 3 in the region of the proximal retention arrangement.
Figure 5:
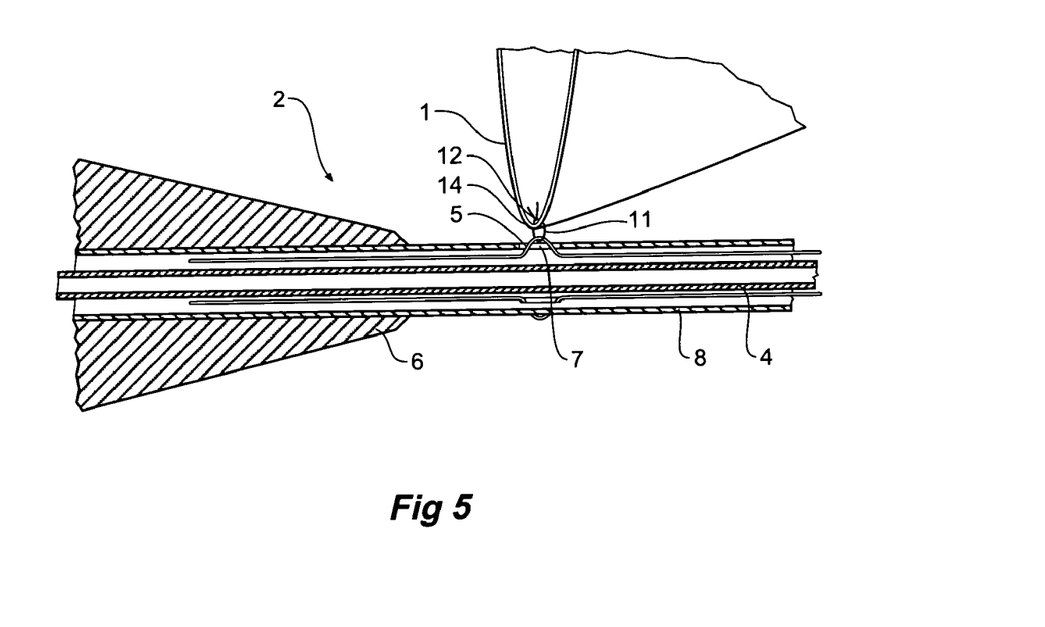
FIG. 5 shows a longitudinal cross section of the embodiment of FIG. 3.

One embodiment of a deployment device and stent graft suitable for the stent graft retention of the present invention is shown in FIGS. 3 to 5.

The deployment device 2 in the region of the proximal retention has a guide wire catheter 4 and a trigger wire catheter 8 coaxially around the guide wire catheter 4.

Trigger wires 5 pass along the annular space 10 between the guide wire catheter 4 and the trigger wire catheter 8 and exit through apertures 7 at the retention points and then re-enter the annular space 10 between the guide wire catheter 4 and the trigger wire catheter 8 and pass into the nose cone 6. The apertures 7 may be equally spaced around the trigger wire catheter or they may be spaced at other selected spacings. In this embodiment there are three apertures 7 spaced at approximately 120 degrees to each other around the circumference of the trigger wire catheter 8.

Where each trigger wire 5 exits out of aperture 7 a thread of suture material or other thread-like material 11 is looped around the trigger wire 5 and is fastened to a bight 14 of the graft material of the stent graft 1 and tied off with a knot 12.

As can particularly be seen in FIG. 3 the stent graft has zig zag Z stents 17 on its inside for the first two stents from the proximal end and then outside zig zag Z stents 19 distally thereof. Each stent is fastened by of sutures 21 to the graft material. Barbs 23 may also be used to encourage retention of the stent grafts against the wall of the aorta. It will be noted that the barbs 23 are distally facing so that pressure of blood flow will cause then to engage more strongly into the wall of the aorta. In some embodiments the thread of suture material or other thread-like material 11 may also be fastened around a portion of the zig zag Z stent 17.

Figure 6:
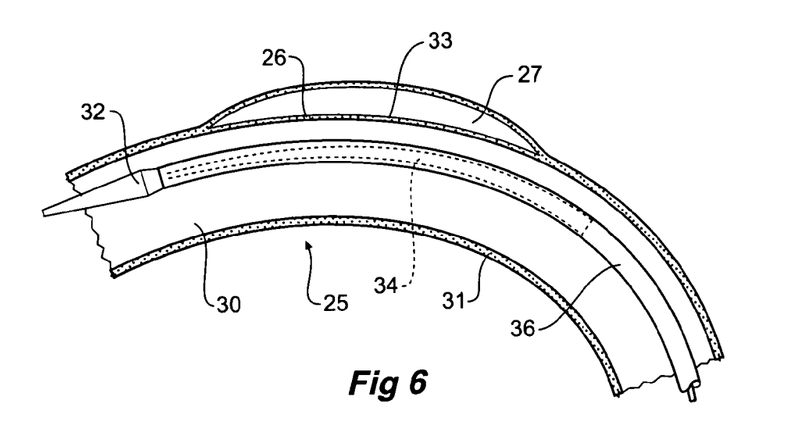
FIGS. 6 to 8 show the various stages of a first embodiment of a stent graft being deployed into a thoracic arch of a patient.
Figure 7:
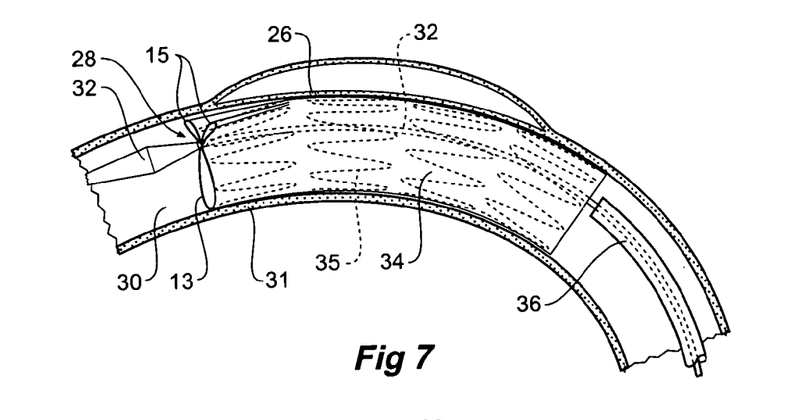
Figure 8:
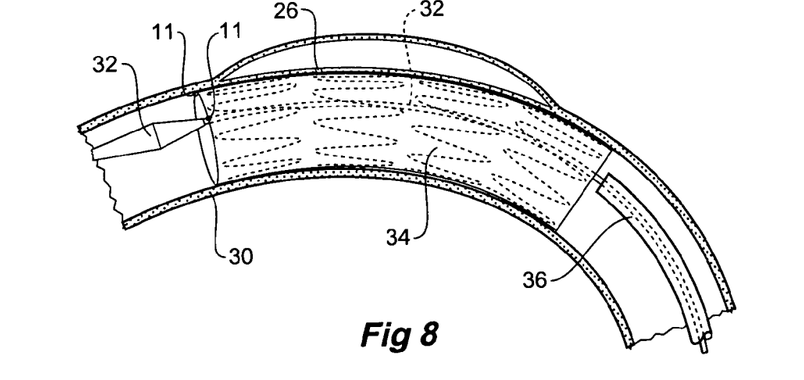

Now looking at the embodiment shown in FIGS. 6, 7 and 8 it will be seen that a thoracic arch 30 of an aorta 25 has an outer curve 33 and an inner curve 31. A stent graft is deployed into the thoracic arch to span, for instance, a tear 26 in the wall of the aorta 25 which has caused an aortic dissection 27.

A deployment device 32 is inserted into the aorta 25 and bent around the thoracic arch 30. Owing to the curvature of the thoracic arch 30 the deployment device 32 will tend to be nearer the outer curve 33 and hence to ensure good engagement of the stent graft on the inner curve, the stent graft retention of the present invention is used.

As can be seen in FIG. 6 the deployment device 32 which is deployed into the thoracic arch 30 has a stent graft prosthesis 34 as shown by the dotted line held within a movable outer sheath 36.

In this embodiment the prosthesis 34 does not have a distal retention mechanism associated with the deployment device and hence when the sheath 36 is withdrawn as shown in FIG. 7 the stent graft under the influence of its self expanding stents 35 opens except at the proximal end 38 where the graft is retained to the deployment device 32 by means of the stent graft retention of the present invention.

As can be particularly be seen in FIG. 7 the larger fold 13 of the stent graft is extended towards the inner side of the curve 31 of the thoracic arch 30 and in this position blood flow can flow through the larger fold 13 and cause it to extend against the inner wall 31 before the stent graft fully engages the outer side of the curve 33. At this stage barbs 23, (see FIG. 3) if present, at the proximal end can engage into the inner wall 31 of the aorta and ensure that that portion of the proximal end of the stent graft is retained against the inside wall of the aorta 25.

As shown in FIG. 8 trigger wires have been released (by a mechanism not shown) so that the stent graft retention has been released and the full circumference of the proximal end of the graft has now fully deployed against the walls of the thoracic arch. Hence there is not the danger of a portion of the circumference of the proximal end of the graft, particularly that engaged against the inner curve 31 folding inwards under the influence of pulsating blood flow and closing off the aorta. Other barbs 23, if present at the proximal end, can then engage the wall of the aorta and ensure that that the entire proximal end of the stent graft is retained against the wall of the aorta. It will be noted that in this embodiment the fastenings 11, which are used to retain the stent graft to the trigger wires, remain on the stent graft.

Figure 9:
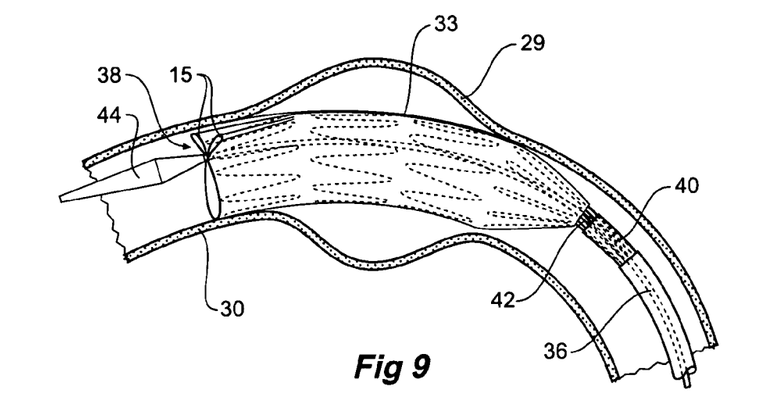
FIGS. 9 to 11 show the various stages of a second embodiment of a stent graft being deployed into the thoracic arch of a patient.
Figure 10:
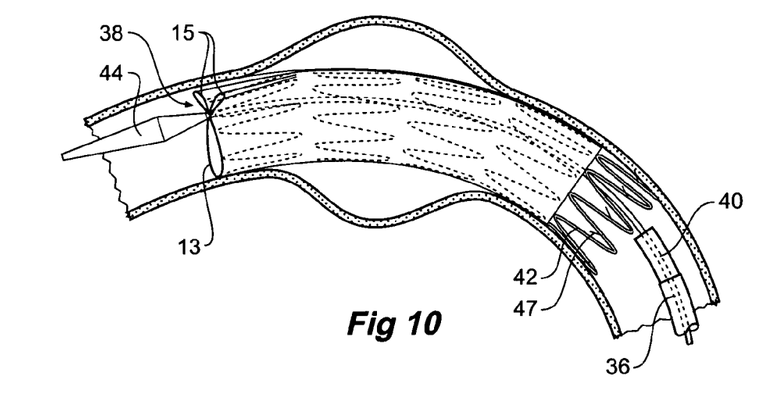
Figure 11:
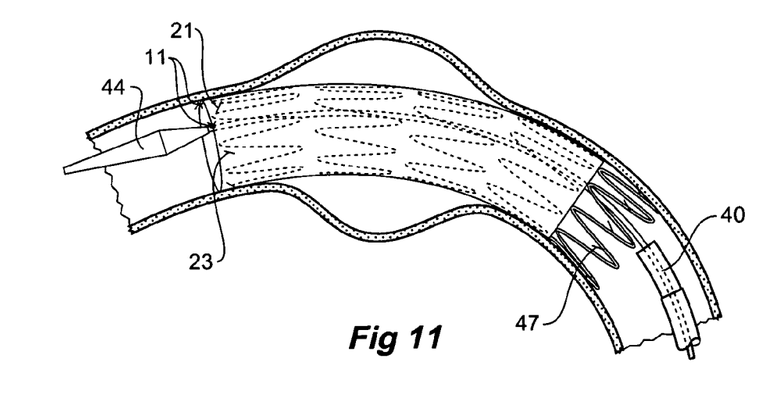

An alternative embodiment of deployment of a stent graft prosthesis retained by the arrangement of the present invention is shown in FIGS. 9, 10 and 11. The stent graft in this embodiment is used to span an aneurysmal sac 29. A number of features are substantially similar to those of FIGS. 6, 7 and 8 and the same reference numerals are used for corresponding items.

The stent graft prosthesis is similar at the proximal end to that depicted in FIGS. 6 to 8, but at its distal end it has a distally extending exposed zig zag Z stent 42. This distally extending exposed stent 42 may have barbs 47. In this embodiment the deployment device is deployed in the aorta 30 in the same manner as shown in FIG. 6 but subsequent deployment of the stent graft prosthesis occurs in two stages.

In a first stage the sheath 36 is withdrawn, as was shown FIG. 7, but as well as the proximal end 38 being retained by the asymmetric proximal stent graft attachment a capsule 40 retains the exposed stent 42 at the distal end.

In the next stage as shown in FIG. 10, the capsule is withdrawn distally so that the exposed stent is released and because of their self expanding nature expand to bear against the walls of the aorta at the distal end of the stent graft prosthesis. The barbs 47 can engage into the wall of the aorta to retain the stent graft in position. At this stage the proximal end 38 of the stent graft prosthesis is still retained to the deployment device by the retention arrangement of the present invention.

It will be noted that the larger fold 13 of the graft is towards the inner side of the curve 31 of the thoracic arch 30 and in this position blood flow can flow through the larger fold 13 and cause it to extend against the inner wall 31 before the graft fully engages the outer side of the curve 33.

Then as shown in FIG. 11, in a similar manner to that shown in FIG. 8, the trigger wires can be released (by a mechanism not shown) so that the stent graft prosthesis is released and the full circumference of the proximal end of the graft can fully deploy against the walls of the thoracic arch. Hence there is not the danger of a portion of the circumference of the proximal end of the graft, particularly that engaged against the inner curve 31 folding inwards and closing off the aorta. Other barbs 23, if present at the proximal end, can then engage the wall of the aorta and ensure that that the entire proximal end of the stent graft is retained against the wall of the aorta. It will be noted that in this embodiment the fastenings 11, which are used to retain the stent graft to the trigger wires, remain on the stent graft. The nose cone 44 of the deployment device can then be withdrawn to the capsule 40 and the deployment device withdrawn.

Throughout this specification various indications have been given as to the scope of the invention but the invention is not limited to only one of these but may reside in two or more of these combined together. The examples are given for illustration only and not for limitation.

What is claimed is:

1. A stent graft prosthesis mounted to a deployment device and adapted to be deployed in a curved lumen, the curved lumen having an inner side and an outer side of the curve, the deployment device including a guide wire catheter, the stent graft prosthesis being temporarily mounted to the deployment device at least one end of the prosthesis by a retention arrangement, the retention arrangement including a retention of the stent graft prosthesis to the guide wire catheter at a plurality of retention points of the circumference of the proximal end of the stent graft prosthesis, there being a greater circumferential distance between two adjacent retention points than other of the points, wherein the retention arrangement includes three retention points so that one larger and two smaller folds of the graft material are formed, the guide wire catheter includes a trigger wire catheter coaxially around the guide wire catheter with trigger wires passing along an annular space between the guide wire catheter and the trigger wire catheter and exiting through apertures in the trigger wire catheter at the retention points and the trigger wires are engaged with the graft material to provide the retention points and the apertures are equally spaced around the trigger wire catheter whereby when the deployment device is deployed in the curved lumen the greater circumferential distance is on the inner side of the curve.

* * * * *

UNITED STATES PATENT AND TRADEMARK OFFICE
CERTIFICATE OF CORRECTION

| | | |
|---|---|---|
| PATENT NO. | : 7,722,657 B2 | Page 1 of 1 |
| APPLICATION NO. | : 10/647642 | |
| DATED | : May 25, 2010 | |
| INVENTOR(S) | : Hartley | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1023 days.

Signed and Sealed this
Eleventh Day of January, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,722,657 B2 | |
| APPLICATION NO. | : 10/647642 | |
| DATED | : May 25, 2010 | |
| INVENTOR(S) | : David Ernest Hartley | |

It is certified that error appears in the above-identified patent and that said Letters Patent is hereby corrected as shown below:

This certificate supersedes the Certificate of Correction issued January 11, 2011.

On the Title Page:

The first or sole Notice should read --

Subject to any disclaimer, the term of this patent is extended or adjusted under 35 U.S.C. 154(b) by 1,508 days.

Signed and Sealed this
Fifteenth Day of February, 2011

David J. Kappos
*Director of the United States Patent and Trademark Office*